(12) United States Patent
Krantz et al.

(10) Patent No.: US 6,969,374 B2
(45) Date of Patent: Nov. 29, 2005

(54) INJECTION SYRINGE AND DISPOSAL CONTAINER FOR INJECTION NEEDLE UNITS

(75) Inventors: Heiko Krantz, Rheinberg (DE); Peter Konrad, Haan (DE)

(73) Assignee: Hager & Werken GmbH & Co. KG, Duisburg (DE)

( * ) Notice: Subject to any disclaimer, the term of this patent is extended or adjusted under 35 U.S.C. 154(b) by 43 days.

(21) Appl. No.: 10/467,235

(22) PCT Filed: Feb. 9, 2001

(86) PCT No.: PCT/DE01/00515

§ 371 (c)(1),
(2), (4) Date: Aug. 6, 2003

(87) PCT Pub. No.: WO02/064197

PCT Pub. Date: Aug. 22, 2002

(65) Prior Publication Data

US 2004/0064108 A1 Apr. 1, 2004

(51) Int. Cl.⁷ .............................................. A61M 5/31
(52) U.S. Cl. ..................................... 604/240; 604/187

(58) Field of Search ................................ 604/181, 187, 604/188, 192, 201, 240

(56) References Cited

U.S. PATENT DOCUMENTS 4,664,653 A * 5/1987 Sagstetter et al. .......... 604/197

* cited by examiner

*Primary Examiner*—Kevin C. Sirmons
(74) *Attorney, Agent, or Firm*—Gudrun E. Huckett

(57) ABSTRACT

An injection syringe has a housing for a medicament ampule and a plunger movable longitudinally in the housing. A holder is connected to the syringe housing for detachably mounting an injection needle unit having a cannula support. The cannula support has a rearward end provided with a radial outer flange ring. A spreading sleeve is provided that is fastened with a cylinder ring on the syringe housing and has several elastic spreading tongues provided with forward ends remote from the cylinder ring and forming an annular cage. The spreading tongues have radial inner noses engaging the flange ring when the injection needle unit is inserted into the holder. An outer sliding sleeve surrounds the spreading sleeve and is movable against a spring force rearwardly. The front end of the sliding sleeve has an annular adjusting element that, upon rearward movement of the sliding sleeve, pushes the spreading tongues radially outwardly.

14 Claims, 3 Drawing Sheets

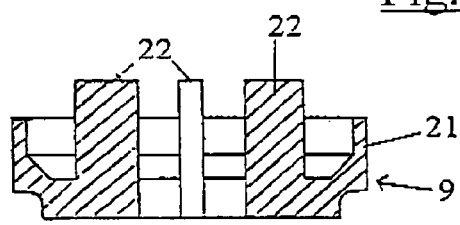
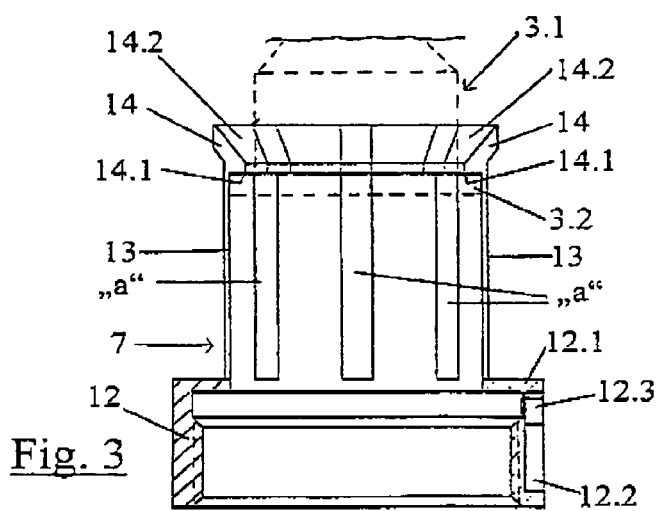
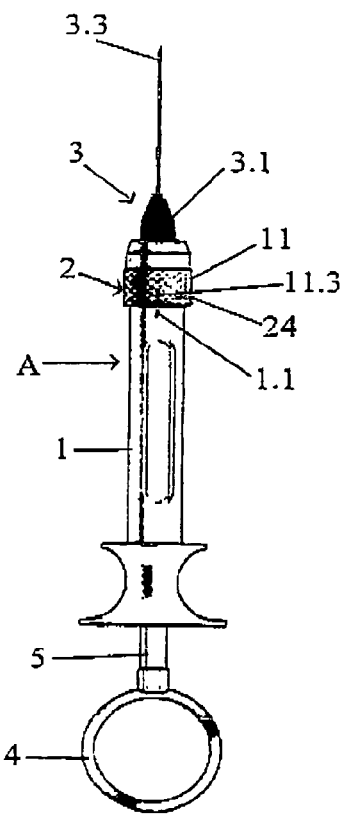
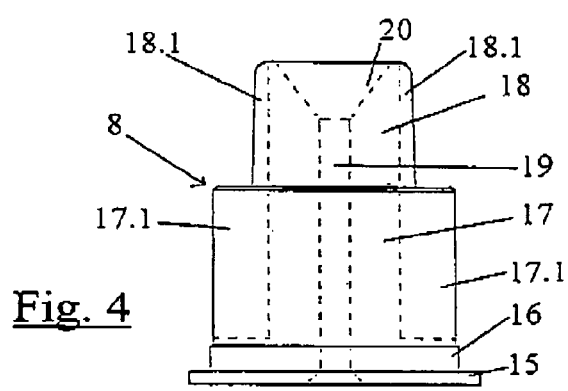

INJECTION SYRINGE AND DISPOSAL CONTAINER FOR INJECTION NEEDLE UNITS

BACKGROUND OF THE INVENTION

The invention relates to an injection syringe as well as a disposal container for receiving injection needle units after their use on such injection syringe.

The injection syringe disclosed in EP 0 787 501 A2 is the starting point for the present invention; it comprises essentially the following elements:

- a housing for receiving a medicament ampule provided with a sealing member;
- a plunger movable in the longitudinal direction of the housing for pushing the sealing member into the medicament ampule;
- a holder for an injection needle unit, wherein the injection needle unit comprises a hub-shaped cannula support detachably insertable into the holder and having at its rearward end a radially outwardly oriented flange ring into which a cannula is inserted so as to project to the front and to the rear;
- a spreading sleeve with elastic spreading tongues that have at their forward end radially inwardly oriented noses which, when the injection needle unit is inserted into the holder, engage behind the flange ring of the cannula support, as well as also radially oriented spreading projections and are mounted with their rearward ends on a cylinder ring fastened on the syringe housing; and
- a sliding sleeve movable to the rear against the force of a spring, wherein the sliding sleeve is designed such that, when it is moved to the rear, it is pushed against the spreading projections so that in this way the spreading tongues are pushed radially outwardly for releasing the injection needle unit.

In this known injection syringe the spreading member has three spreading tongues provided at their rearward ends facing the cylinder ring with spreading projections that are radially inwardly oriented. The sliding sleeve is provided with radially outwardly oriented projections which upon movement of the sliding sleeve in the direction of the syringe housing press against the spreading projections provided on the spreading tongues so that the spreading tongues all together are moved outwardly and release in this way the injection needle unit.

The spreading projections provided at the rearward ends of the spreading tongues as well as the sliding sleeve provided with the outwardly oriented projections cause an increased expenditure that also makes manufacture more difficult, aside from the fact that only three spreading tongues cannot always ensure a safe insertion and fixation of the injection needle unit in the holding device.

SUMMARY OF THE INVENTION

The invention has the object to provide an injection syringe whose holder for the purpose of a simple manufacture is of a simpler configuration with respect to construction aspects than the known injection syringe, wherein additionally also a safe fixation of the injection needle unit in the holder is to be ensured.

As a solution to this object the injection syringe according to the invention is characterized in that the spreading member has at least four spreading tongues forming an annular cage and that the sliding sleeve at its forward end has an annular adjusting element with which the spreading tongues are pushed radially outwardly upon rearward movement of the sliding sleeve.

Overall, the sliding sleeve is a body having rotational symmetry which can be manufactured relatively simply in comparison to the sliding sleeve that is used in the known syringe and is provided with a number of outwardly oriented projections matching the number of spreading tongues. In the holder according to the invention, the projections or wider portions of the spreading tongues cooperating with the outwardly oriented projections of the sliding sleeve are not required.

BRIEF DESCRIPTION OF THE DRAWINGS

The invention will be explained in the following with the aid of the drawings:

FIG. 1 shows a side view of the injection syringe according to the invention with an injection needle unit inserted therein;

FIG. 3 shows the spreading sleeve in an axial section;

FIG. 4 shows a side view of the guide member;

FIG. 5 shows a section view of the needle ejector;

DESCRIPTION OF PREFERRED EMBODIMENTS

Figure 2:
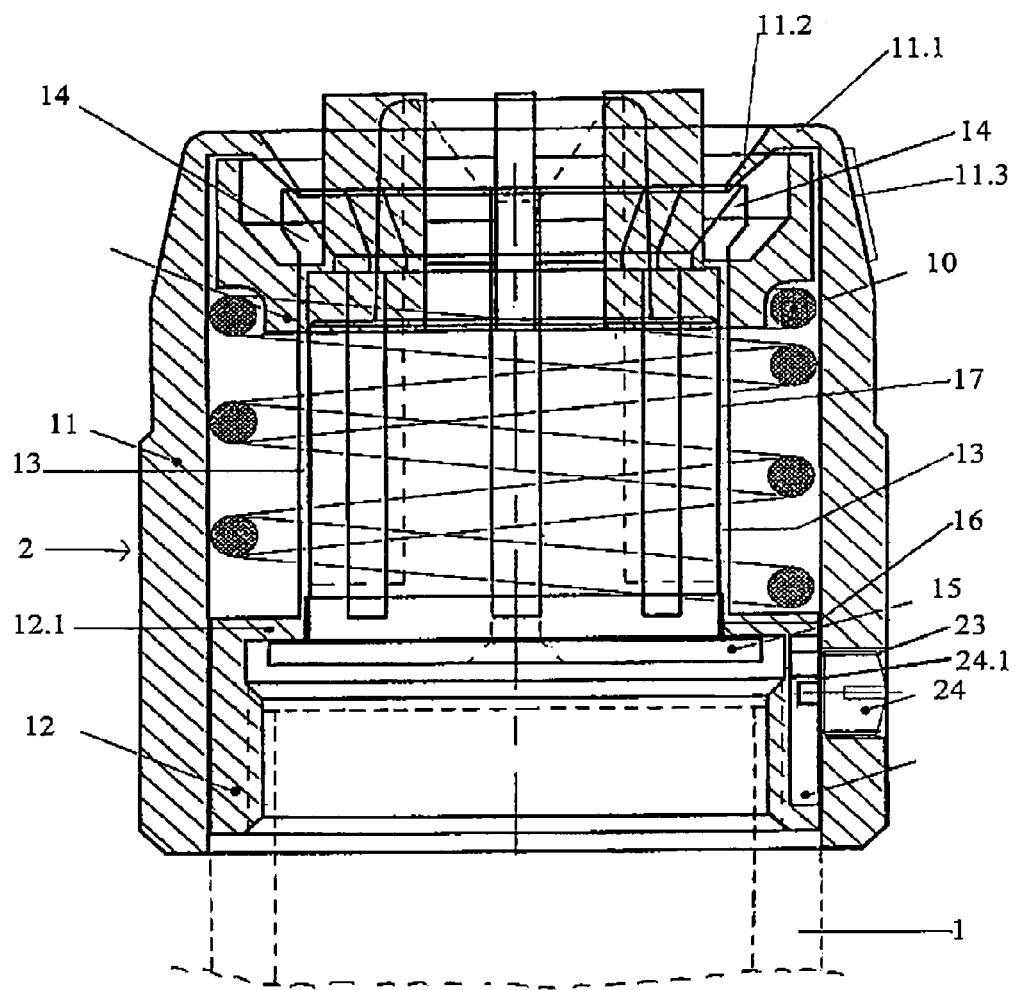
FIG. 2 shows an axial section of the holder for the injection needle unit that is configured according to the invention and is screwable onto the syringe housing, which holder comprises substantially a spreading sleeve, a tubular guide member for the injection needle unit, a needle ejector as well as an outer sliding sleeve.

The injection syringe A illustrated in FIG. 1 has a housing 1 for receiving a medicament ampule that is of a conventional design and therefore not illustrated; it is closed at the rearward end by a sealing member and at its forward end by a septum. Into the forward end of the injection syringe A, the cannula attachment 3 of an injection needle unit B is detachably inserted by means of the holder 2 to be described in the following; the injection needle unit has a rearward cannula section that can be punched through the septum of the medicament ampule. A rod 5 that can be pushed by means of a handle 4 into the housing 1 supports at its leading end a plunger (not illustrated) which upon insertion of the rod 5 into the housing pushes the sealing member, closing off the rearward end of the ampule, into the ampule so that the medicament contained in the ampule can be injected by means of the outer cannula injection section 6 into a patient.

The injection syringe described by means of FIG. 1 corresponds with respect to its basic configuration to the injection syringe described in EP 0 787 501. The syringe of the present invention differs from the known injection syringe essentially by the configuration of the holder 2 illustrated in FIG. 2.

The holder 2 is comprised in detail of the spreading sleeve 6, illustrated as an individual part in FIG. 3, into which the cannula attachment 3, indicated in dashed lines, is inserted; a tubular guide member 8 (see FIG. 4) insertable from below into the spreading sleeve 7 and preferably inserted with press-fit; a needle ejector 9 illustrated in FIG. 5 which is movable against the force of a spring 10 relative to the centering sleeve 7; as well as an outer sliding sleeve 11 that is movable relative to the spreading sleeve 7 screwed onto the housing 1 as will be described in the following.

The spreading sleeve 7 is comprised of a cylinder ring 12 having an inner thread; an inwardly oriented flange ring 12.1 adjoins the upper end of the cylinder ring. On this annular flange 12.1, several, preferably eight, elastic spreading tongues 13 are provided that form an annular cage. On the forward free end of each spreading tongue 13, a holding and guiding member 14 forming a radially inwardly projecting nose 14.1 is provided which has a guide surface 14.2 which extends at a slant inwardly from the top to the bottom.

The guide surfaces 14.2 of all spreading tongues 13 form a conical surface interrupted by the gaps a between neighboring spreading tongues 13.

The guide member 8, which is illustrated in FIG. 4 and is inserted from below into the spreading sleeve 7, for example, by press-fit, comprises a flange ring 15 resting against the underside of the flange ring 12.1; an adjusting and centering collar 16 resting against the inner edge of the flange ring 12.1; a central cylinder section 17 having a diameter which is reduced relative to the adjusting ring 16; as well as an upper cylinder section 18. The guide member 8 is provided with a continuous central bore 19 into which a conical bore 20 opens at the upper end of the upper cylinder section 18.

The central and upper cylinder sections 17 and 18 are provided, for example, with four recesses 17.1 and 18.1 that are radially inwardly oriented and extend in the axial direction; in the final mounted state of the holder 2, they are positioned opposite the gaps a located between the spreading tongues 13 or aligned with them.

The needle ejector 9 is comprised of a ring 2.1 on which, for example, four radially inwardly oriented sheet-shaped ejector wings 2.2 are arranged which project past the upper side of the ring 21. The arrangement of the ejector wings 2.2 is such that during axial movement of the needle ejector 9 they are guided in the recesses 17.1 and 18.1 through the gaps a between the cylinder tongues.

The sliding sleeve 11 has essentially the shape of a cylinder bushing having at the upper end an inwardly oriented flange ring 11.1 against whose underside the upper rim of the ring 21 of the needle ejector 9 is pushed by the spring 10. A conical ring 11.2, which is oriented at a slant inwardly and to the rear and has of tongue-shaped cross-section, adjoins the flange ring 11.1. The lower edge of the conical ring projects into the conical surface formed by the guide surfaces 14.2 of the spreading tongues 13.

The threaded bushing 12 of the spreading sleeve 7 is provided at its outer periphery with an axial groove 12.2; a groove section 12.3 extending in the circumferential direction of the threaded bushing adjoins an upper end of the axial groove. The sliding sleeve 11 is provided with a radially oriented threaded bore 23 for receiving a stud screw 24 which has a projection 24.1 projecting into the groove 12.2 or 12.3. When the projection 24.1 projects into the circumferential groove 12.3, the sliding sleeve 11 is secured against axial movement. This state corresponds to the state of use of the injection syringe A with the injection needle unit B inserted into the holder 2. This state is indicated by the markings 1.1 and 11.3, aligned with one another, on the outer circumference of the sliding sleeve 11 and on the outer circumference of the syringe housing 1, respectively. In FIG. 1 the markings 1.1 and 11.3 indicate the state in which the projection 24.1 of the stud screw 24 is positioned at the end of the circumferential groove 12.3 so that the sliding sleeve 11 is secured against axial movement.

For insertion of an injection needle unit into the holder 2, first the rearward cannula section, not illustrated, is inserted through the conical bore 20 into the central bore 19 until the radially outwardly oriented flange ring 3.2 of the cannula support 3.1 rests against the guide surfaces 14.2 of the spreading tongues 13. By further inward pushing of the cannula support 3.1 into the holder 2, the flange ring 3.2 of the cannula support 3.1 moves along the guide surfaces 14.2 so that the spreading tongues 13 are pushed outwardly until the flange ring 3.2 has past the holding and guiding member 14 so that the spreading tongues 13 can return elastically into their initial position and the flange ring 3.2 assumes a position underneath the noses 14.1 as illustrated in FIG. 3.

The underside of the flange ring 3.2 in this state is supported on the ring shoulder surrounding the upper cylinder section 1.8 of the guide member 8; the ring shoulder is formed by the free upper side of the central cylinder section 1.7.

The injection needle unit 3 is thus secured against axial movement in both directions as long as the sliding sleeve 11 is in the position illustrated in FIG. 1.

For removing or ejecting the injection needle unit 3 after its use, the sliding sleeve 11 is rotated relative to the housing 1 in the direction of the marking 1.1 provided on the housing 1 so that the projection 23 of the stud screw 24 is adjustable along the circumferential groove 12.3 in the direction toward the axial groove 12.2. As soon as the stud screw projection 23 reaches the area of the axial groove 12.2 and the system is thus "unlocked", the sliding sleeve 11 can be moved to the rear counter to the spring force of the restoring spring 10 positioned between the needle ejector 9 and the annular flange 12.1 of the spreading sleeve 7. This causes the conical ring 11.2, arranged at the forward end of the sliding sleeve 7 at a slant inwardly and to the rear, to be pushed against the guide surfaces 14.2 provided on the spreading tongues 13 and extending at a slant inwardly; in this way, upon further movement of the sliding sleeve 11 to the rear the spreading tongues 13 are pushed outwardly. Accordingly, the flange ring 3.2 provided on the cannula support 3.1 will be released by the securing and guiding members 14 or their noses 14.1 so that the cannula attachment 3.1 and thus the entire injection needle unit 3 can be ejected from the holder 2 under the effect of the restoring spring 10 acting on the needle ejector 9.

Figure 6:
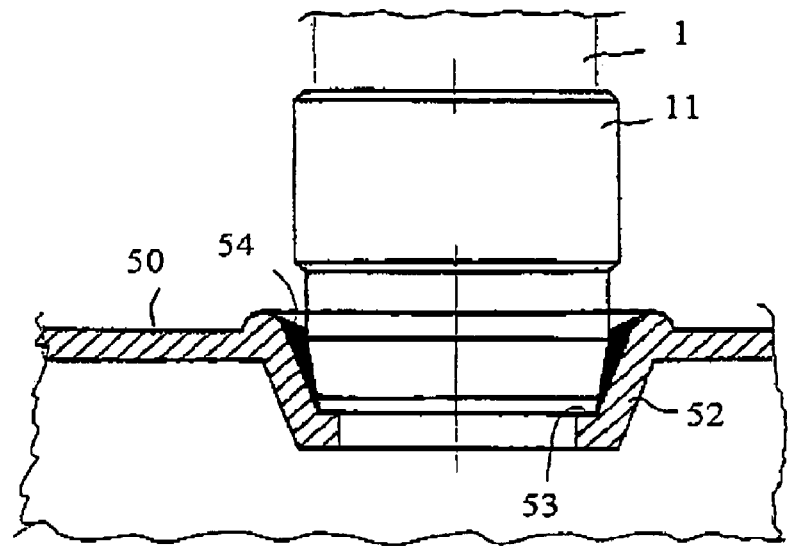
FIG. 6 shows in a sectional view a portion of the cover of a disposal container.
Figure 7:
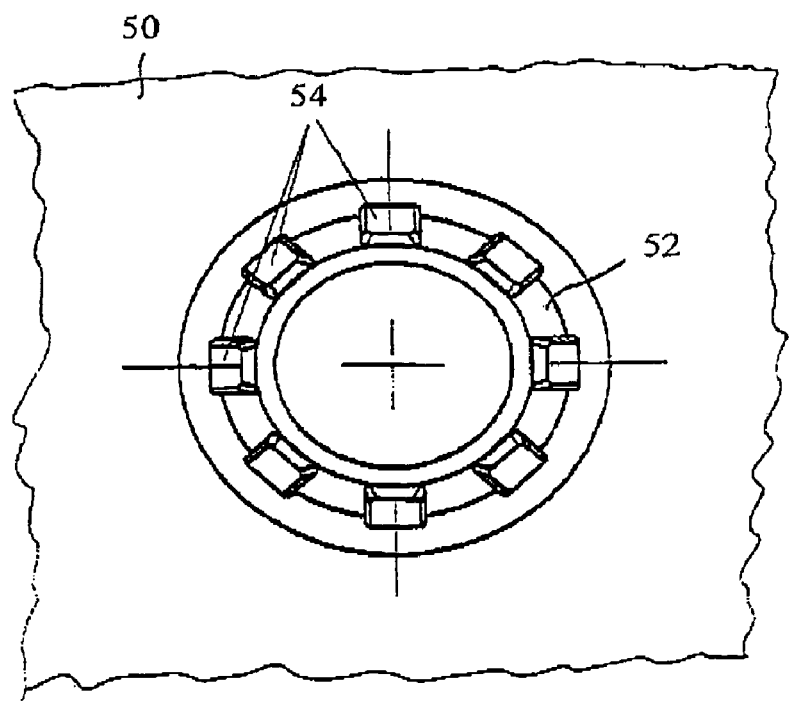
FIG. 7 shows a partial plan view onto a cover according to FIG. 6.

This ejection is realized preferably into a disposal container whose cover 50 illustrated in FIGS. 6 and 7 has a circular opening adjoined by a downwardly conically tapering pipe section 52 having at its lower edge an inwardly oriented ring flange 53. On the inner wall of the pipe section 52 at least one holding element 54 is provided which is capable of securing the sliding sleeve 11 against rotation relative to the disposal container and thus also relative to the injection syringe when the sliding sleeve 11 of an injection syringe is inserted from above into this pipe section 52.

According to FIG. 7, on the inner wall of the pipe section 52 preferably eight holding elements in the form of clamping stays 54 extending along the surface lines of the pipe section 52 are provided.

The forward end of the sliding sleeve 11 has a section conically tapering in the direction toward the forward sliding sleeve; at its side at least one rib 11.3 insertable between the clamping stays 54 is provided.

For a contact-free ejection of the used injection needle unit 3 the injection syringe with its sliding sleeve 11 is inserted into the pipe section 52 of the disposal container, not illustrated otherwise, so that the sliding sleeve 11 is secured within the pipe section 52 against rotation.

By rotating the housing 1 the system is "unlocked" in the way described above so that the injection syringe with its spreading sleeve 7 is moved in the direction of the disposal container so that the spreading tongues 13 are pushed in the above described way by the conical ring 11.2 outwardly and, in this way, release the injection needle unit 3 or its cannula attachment 3.1.

What is claimed is:

1. An injection syringe comprising:
    a syringe housing, having a forward end and a rearward end, for receiving a medicament ampule that is provided with a sealing member;
    a plunger movable in a longitudinal direction of the syringe housing for pressing the sealing member into the medicament ampule;
    a holder, connected to the forward end of the syringe housing, for receiving an injection needle unit, wherein the injection needle unit comprises a hub-shaped cannula support detachably insertable into the holder, wherein the cannula support has a rearward end provided with a radially outwardly oriented flange ring, and wherein a cannula is inserted into the cannula support so as to project to the front and to the rear of the cannula support;
    a spreading sleeve comprising a cylinder ring fastened on the syringe housing and further comprising elastic spreading tongues provided with forward ends remote from the cylinder ring;
    wherein the spreading tongues have radially inwardly oriented noses engaging the flange ring when the injection needle unit is inserted into the holder;
    wherein the spreading sleeve comprises at least four of the spreading tongues forming an annular cage;
    an outer sliding sleeve surrounding the spreading sleeve and movable against a force of a spring in a rearward direction away from the forward end of the syringe housing;
    wherein the sliding sleeve has a front end provided with an annular adjusting element, wherein the adjusting element, upon movement of the sliding sleeve in the rearward direction, pushes the spreading tongues radially outwardly.

2. The injection syringe according to claim 1, wherein the forward ends of the spreading tongues have guide surfaces extending from a free end radially inwardly at a slant toward the cylinder ring.

3. The injection syringe according to claim 2, wherein the front end of the sliding sleeve has a slantedly inwardly and rearwardly oriented conical ring, wherein the conical ring is tongue-shaped in cross-section and interacts with the guide surfaces of the spreading tongues.

4. The injection syringe according to claim 1, wherein the spreading sleeve has eight of the spreading tongues.

5. The injection syringe according to claim 1, further comprising a needle ejector guided within the sliding sleeve and comprising an ejector ring surrounding the spreading tongues; wherein the needle ejector is movable relative to the spreading tongues against the force of the spring, wherein the ejector ring has on its inner sides radially inwardly oriented ejector wings engaging gaps between the spreading tongues and projecting past a topside of the ejector ring.

6. The injection syringe according to claim 5, wherein the spring is supported between an underside of the ejector ring and a flange ring of the spreading sleeve, wherein the flange ring adjoins the cylinder ring and has an inner edge, wherein the spreading tongues are connected to the inner edge.

7. The injection syringe according to claim 1, further comprising a central tubular guide member for guiding a cannula section of the cannula insertable into the ampule, wherein the guide member is fixedly attached to the spreading sleeve.

8. The injection syringe according to claim 1, further comprising a screw threaded into a threaded bore of the sliding sleeve, wherein an outer circumference of the spreading sleeve has an axial groove and wherein the screw engages the axial groove, wherein a length of the axial groove determines a travel stroke of the sliding sleeve.

9. The injection syringe according to claim 8, wherein the outer circumference of the sliding sleeve has a groove section, extending in a circumferential direction of the spreading sleeve and adjoining a forward groove end of the axial groove, wherein the groove section enables a rotary movement of the sliding sleeve relative to the spreading sleeve.

10. The injection syringe according to claim 9, further comprising markings arranged on the outer circumference of the sliding sleeve and on an outer circumference of the syringe housing, respectively, wherein the markings indicate a rotational position of the sliding sleeve relative to the syringe housing in which rotational position an axial movement of the sliding sleeve is not possible.

11. A disposal container for receiving an injection needle unit after having been used on an injection syringe according to claim 1, the disposal container comprising:
    a cover having a circular opening;
    a pipe section adjoining the circular opening and conically tapering in an axial direction of the pipe section away form the circular opening;
    wherein the pipe section has an inner wall provided with at least one holding element, wherein the at least one holding element is configured to secure the sliding sleeve against rotation relative to the injection syringe when the sliding sleeve of the injection syringe is inserted via the circular opening into the pipe section.

12. The disposal container according to claim 11, wherein the inner wall of the pipe section has eight of the holding elements, wherein the holding elements are clamping stays extending along surface lines of the pipe section.

13. The disposal container according to claim 11, wherein the lower pipe section has a lower edge remote from the circular opening, wherein an inwardly oriented annular flange adjoins the lower edge of the pipe section.

14. A combination of the injection syringe according to claim 1 and of the disposal container according to claim 11, wherein the front end of the sliding sleeve has a conical section conically tapering toward an end face of the front end of the sliding sleeve, wherein the conical section has an outer side provided with at least one rib for contacting the at least one holding element.

* * * * *